(12) United States Patent
Holloway

(10) Patent No.: US 6,230,328 B1
(45) Date of Patent: May 15, 2001

(54) JEWELER PLATINUM WELDING EYE-PROTECTION DEVICE HAVING A CLIP-ON MOUNT

(76) Inventor: Michael Gary Holloway, 3843 10th Ave. South, Minneapolis, MN (US) 55407

( * ) Notice: Subject to any disclaimer, the term of this patent is extended or adjusted under 35 U.S.C. 154(b) by 0 days.

(21) Appl. No.: 09/476,952

(22) Filed: Jan. 3, 2000

Related U.S. Application Data

(63) Continuation-in-part of application No. 09/062,092, filed on Apr. 17, 1998, now Pat. No. 6,012,163.

(51) Int. Cl.$^7$ .................................................. A61F 9/06
(52) U.S. Cl. ........................................... 2/8; 219/147
(58) Field of Search ........................ 2/8, 432, 424, 2/9, 10; 359/802; 219/147

(56) References Cited

U.S. PATENT DOCUMENTS

| | | |
|---|---|---|
| 1,777,701 | 10/1930 | Ramstein . |
| 2,055,117 | 9/1936 | Bowers . |
| 2,105,071 | 1/1938 | Bowers . |
| 2,461,548 | 2/1949 | Huntsman . |
| 2,526,582 | 10/1950 | Rowan . |
| 2,588,553 | 3/1952 | McWethy . |
| 2,658,200 | 11/1953 | Bowers, Sr. . |
| 3,016,542 * | 1/1962 | Lindblom ............................ 2/432 |
| 3,325,824 | 6/1967 | Donegan . |
| 3,414,347 | 12/1968 | Stoltze . |
| 3,444,561 | 5/1969 | Boyer . |
| 3,572,931 | 3/1971 | Adler . |
| 3,597,041 | 8/1971 | Frantz et al. . |
| 4,109,132 | 8/1978 | Butoi . |
| 6,012,163 * | 1/2000 | Holloway ............................... 2/8 |

OTHER PUBLICATIONS

Tools & Equipment 1997 catalog, pp. 88 and 169, Rio Grande Tools & Equipment®, 7500 Bluewater Road NW, Albuquerque, New Mexico 87121–1962.

GV97: Tools, Supplies and Equipment for Technicians and Craftsmen, pp. 31, 157, and 158, Stebgo Metals, Inc., Precious Metals Specialists, P.O. Box 7, So. St. Paul, Minnesota 55075–0007 (® 1997 Grobet File Company of America, Inc.).

1998 Catalog: Tools, Supplies, and Equipment for Jewelry Manufacturing, p. 7, Kingsley North, Inc., 910 Brown Street, P.O. Box 216, Norway, Michigan 49870.

* cited by examiner

Primary Examiner—Peter Nerbun
(74) Attorney, Agent, or Firm—Merchant & Gould P.C.

(57) ABSTRACT

An eye protection device for use in the welding of platinum jewelry items under magnification of a visor containing lens includes a pair of opposing support arms attached to a mounting bracket for attachment to the image magnification visor. A filter frame unit containing a welding filter screen is rotatably coupled to the opposing support arms to permit the filter frame to move between a stored, stowed, and a deployed position. The support arms are configured to hold the filter frame in the stowed position in a manner such that the frame can be moved to the deployed position with a quick movement of a user's head while worn.

7 Claims, 5 Drawing Sheets

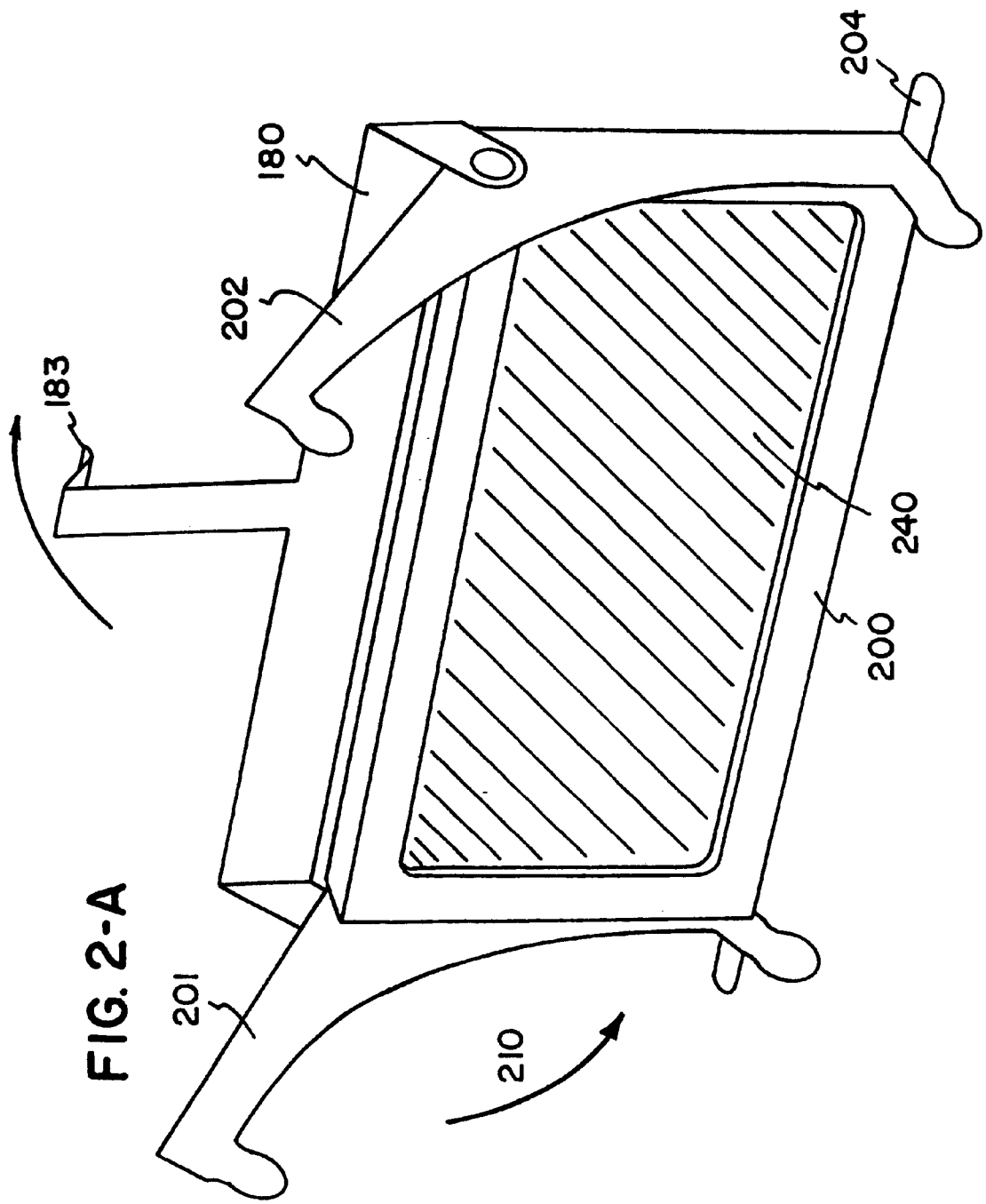
FIG. 2-A

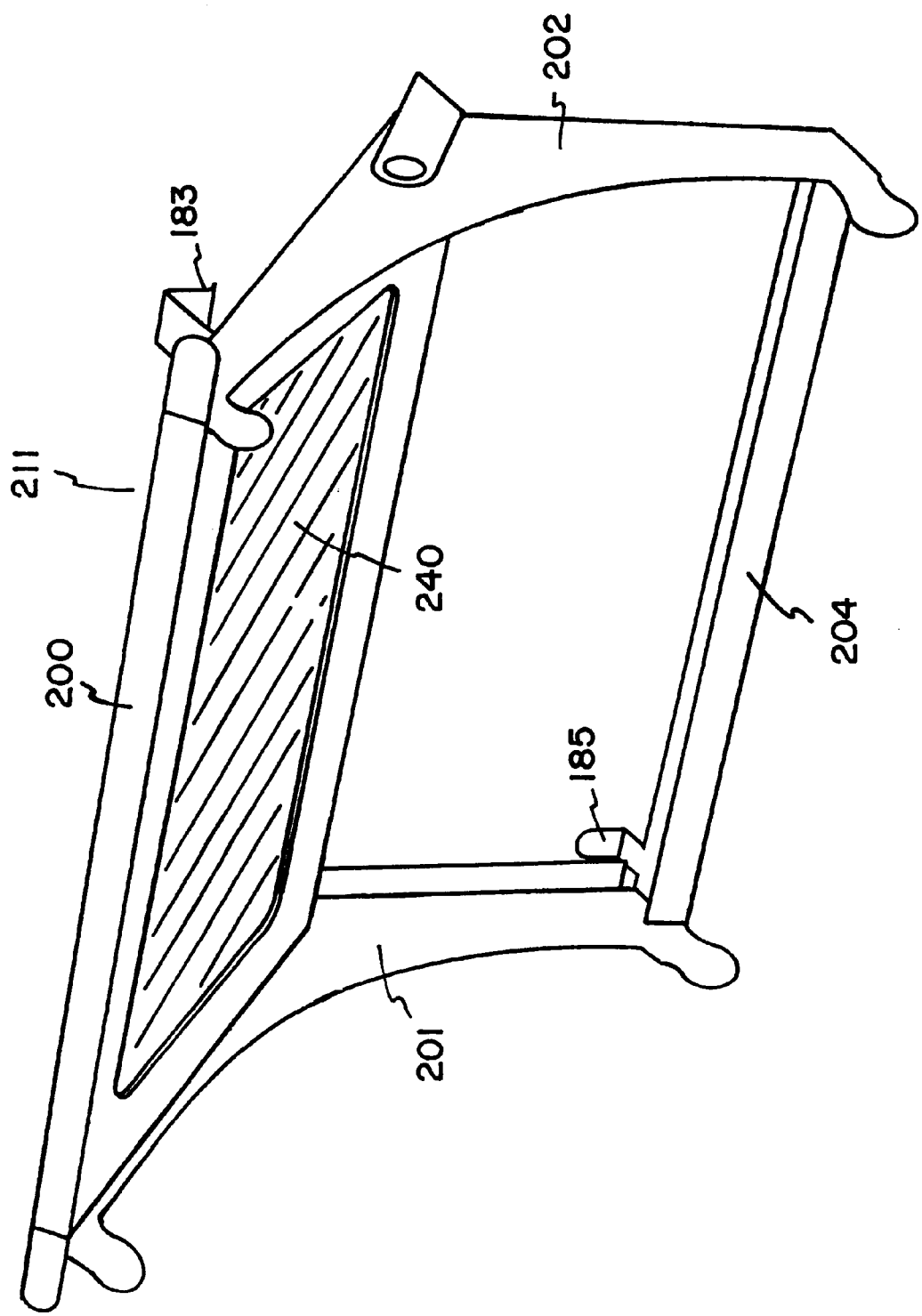
FIG. 2-B

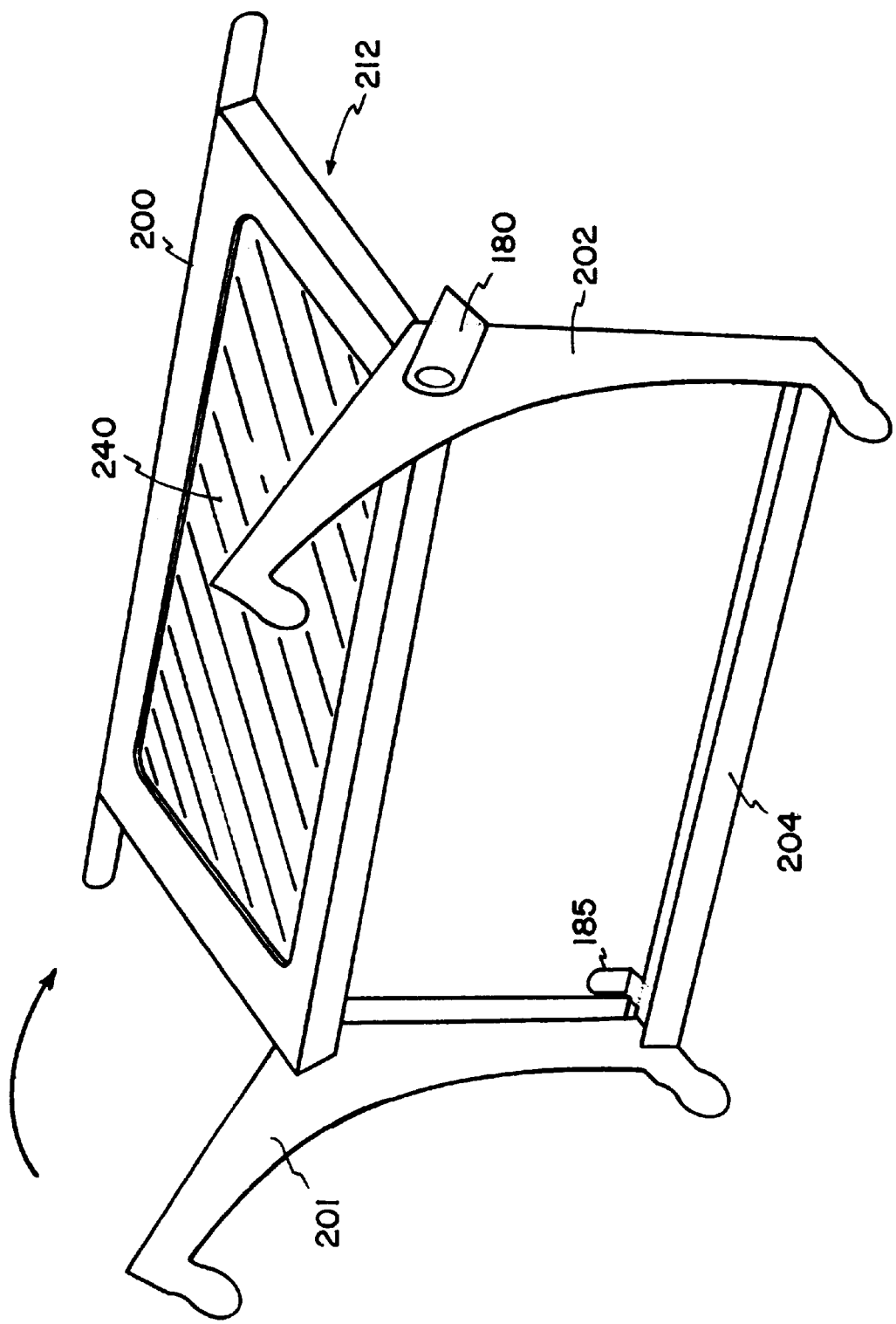

US 6,230,328 B1

JEWELER PLATINUM WELDING EYE-PROTECTION DEVICE HAVING A CLIP-ON MOUNT

This is a continuation-in-part of application Ser. No. 09/062,092, filed Apr.17, 1998, now U.S. Pat. No. 6,012,163.

FIELD OF THE INVENTION

The present invention relates to eye protection systems. More particularly, the present invention relates to visors for protecting jeweler's vision while welding platinum items.

BACKGROUND OF THE INVENTION

An increasing number of men and women are choosing platinum as the material to construct their jewelry. This increase is especially true with respect to engagement rings and wedding bands when compared to only a few years ago. The increased sales of platinum jewelry items has created the need for jewelers to work more often with platinum as these items are manufactured, altered, and/or repaired to meet the specific needs of the purchasers.

Platinum, however, possesses characteristics which make these tasks more challenging to jewelers who generally perform similar tasks on items made from either gold or silver. One such characteristic is that platinum glows a blindingly bright color while being welded. This blinding effect is exacerbated when a jeweler uses image magnification to perform intricate detail work required by many jewelry items.

Jewelers have been forced by these vision problems to wear welding glasses or goggles in order to work on platinum. Presently available glasses and goggles, however, have significant drawbacks. First, these glasses and goggles must be put on before the jeweler is ready. This fact causes the initial work to be performed through the dark lens before these lens are needed. If the jeweler begins the welding process without the glasses or goggles in place, he or she must typically put the torch and/or poker used in the welding process down, and thus stop the process, in order to adjust the glasses. Additionally, these glasses and goggles are not generally well integrated with the image magnifying visors typically worn by jewelers in order to work on intricate items. This lack of integration aggravates the problems associated with donning the darkened glasses as the glasses need to be worn along with the magnifying visor. Of course, the magnification of the work area increases the visual effect of the glowing platinum which contributes to the need for the darker lens.

SUMMARY OF THE INVENTION

To overcome the limitations in the prior art, and to overcome other limitations that will become apparent upon reading and understanding the present specification, a preferred embodiment constructed in accordance with the principles of the present invention includes an eye protection apparatus for use in welding platinum which is designed to allow quick attachment and detachment to the exterior of a commonly worn jewelers style magnifying visor, which is worn like a headband above the eye area. A rotatable bracket secures the eye protection device to the magnifying visor with a snapping friction bracket. The device is primarily a welding filter lens enclosed within a frame, which is rotatably suspended between two opposing support arms, which allow the rotatable filter frame to be stowed in any of three positions—the stored position, the stowed position, the deployed position. Additionally, the rotatable filter frame can be moved from the stowed position (supported above the wearer's field of view by the opposing arms) into the deployed position (protecting the wearer's field of view) by using a slight forward and downward snap of the wearer's head, thus permitting the freedom of the user's hands to manipulate a torch in one hand and a welding poker in the other.

Other embodiments of a system in accordance with the principles of the invention may include alternative or optional additional aspects. These aspects and various other advantages and features which characterize the invention are pointed out with particularity in the claims annexed hereto and form a part hereof. However, for a better understanding of the invention, its advantages, and the objects obtained by its use, reference should be made to the drawings which form a further part hereof, and to the accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIGS. 2a–2c illustrate example embodiments of the present invention in its deployed, stowed and stored positions.

DETAILED DESCRIPTION OF EXAMPLARY EMBODIMENTS

The present invention has been found to be generally advantageous in providing eye protection to users, and has been found to be particularly advantageous in providing eye protection to jewelers while welding platinum items viewed under magnification. An appreciation of various aspects of the invention is best gained through a discussion of various application examples in such an environment.

Figure 1:
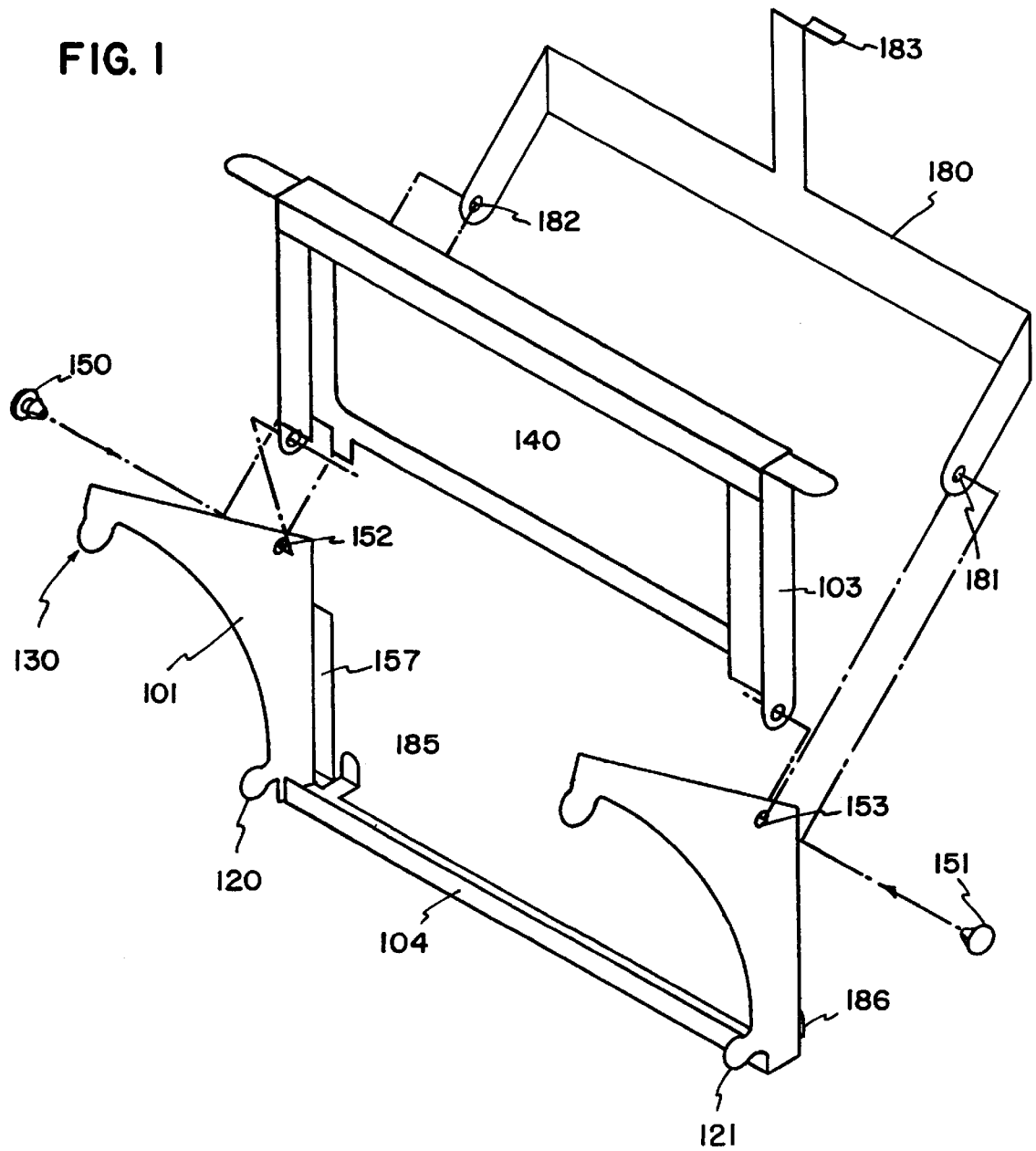
FIG. 1 illustrates an example embodiment of the present invention comprising two opposing support arms rotatably connected to a filter frame.

Turning now to the drawings, FIG. 1 illustrates a flip down eye filter apparatus according to an example embodiment of the present invention. The present invention comprises two opposing support arms 101 and 102 connected together by a securing bracket 104. The securing bracket is configured as U-shaped providing a surface area on which attachment through-holes 152 and 153 can be located. The center of the U-shaped bracket is open to permit a line of sight through the filter when worn by an individual.

The two support arms comprise two L-shaped projection members 101 and 102 which extend both upward and outward from the securing bracket 104. A pair of restraining friction tabs 130 and 131 are located on the outward end of each of the support arms. These restraining tabs extend downward in the direction towards a pivoting filter frame 103. Each of these tabs are shaped such that they each engage the outward edge of the filter frame 103 to hold the filter frame 103 in its stowed position.

In one particular embodiment, the restraining tabs 130 and 131 are appendages extending from the support arms 101 and 102 which are arranged and configured such that they engage the respective sides of the filter frame 103 to hold the frame in place. The filter frame 103 can be rotated through the support arms to allow the frame to rest on top of the entire assembly. The filter frame is out of the way of a user in this stored position when the darkened filter screen is not needed. See FIG. 2C. The particular shape of these tabs, of course, can be changed in alternate embodiments to include other appendage and indent coupling arrangements which provide a frictionally-generated restraining force sufficient to hold the filter frame in the stowed position. Additionally, magnetic material could also be added to one or more of these tabs to supplement the frictional restraining force.

A pair of restraining tabs 120 and 121 are also located on the bottom edge of the support arms 102 and 103 proximate to the bracket 104. The outward edges of the filter frame 103 also engage these second pair of restraining tabs to hold the filter frame 103 in its deployed position. The second pair of restraining tabs are shaped, and function, similarly to the previously described tabs 130 and 131.

The filter frame 103 is rotatably coupled to the two opposing support arms 102 and 103 to create an axis of rotation 160 at two attachment points 150 and 151. In one particular embodiment, the filter frame 103 possesses two attachment pins 150 and 151 which pass through holes 152 and 153 located in the two support arms 101 and 102. The filter frame pivots about this axis of rotation 160 to permit the frame to swing between the stowed position, where the filter frame engages the restraining tabs 130/131 and the deployed position, where the mating tabs engage the restraining tabs 120/121. Alternatively, the filter frame can be rotated out of the way of a user by moving the filter frame 103 through the support arms 101 and 102 to rest upon the top of the assembly in its stored position.

Within the filter frame, a welding filter screen 140 is placed. When the filter frame is in the deployed position, the useris line of sight will pass through the U-shaped mounting bracket 104 and through the filter screen 140. In one particular embodiment, the filter screen is constructed using a number 6 shade welding screen. Of course, this screen can be constructed using any other desired shade.

The apparatus also has a moveable mounting clip 180 that is generally U-shaped having mounting through holes 181 and 182 located on each end of the mounting clip 180. The mounting clip is coupled to the apparatus using the attachment pins 150 and 151 that are used to secure the filter frame 103 to support arms 101 and 102. The mounting clip is typically positioned in a direction opposite the direction that the support arms 101 and 102 point.

The mounting clip 180 possesses a projection member 184 having a clipping device 183 at a first end. The projection member 184 is coupled to the u-shaped mounting clip at a second end of the projection member 184. The projection member is typically located at a point equal distance between the support arms 101 and 102 when the mounting clip 180 is coupled to the apparatus.

The securing bracket 104 possesses a pair of attachment tabs 185 and 186 located about each end of the securing bracket near each of the two support arms 101 and 102. These attachment tabs 185 and 186 are used in conjunction with the clipping device 183 on the projection member 183 to secure the apparatus to an image magnifying visor as shown in FIG. 3.

FIGS. 2a, 2b, and 2c show the frame filter 200 located in the stowed 210, deployed 211, and stored positions 212 respectively. FIG. 2a shows how the support arms 201 and 202 extend both outward and upward from the mounting bracket 204. The purpose for extending the support arms both outward and upward is to ensure that the stowed position 212 places the filter frame 200, and its filter screen 240, completely out of the useris field of view.

Figure 3:
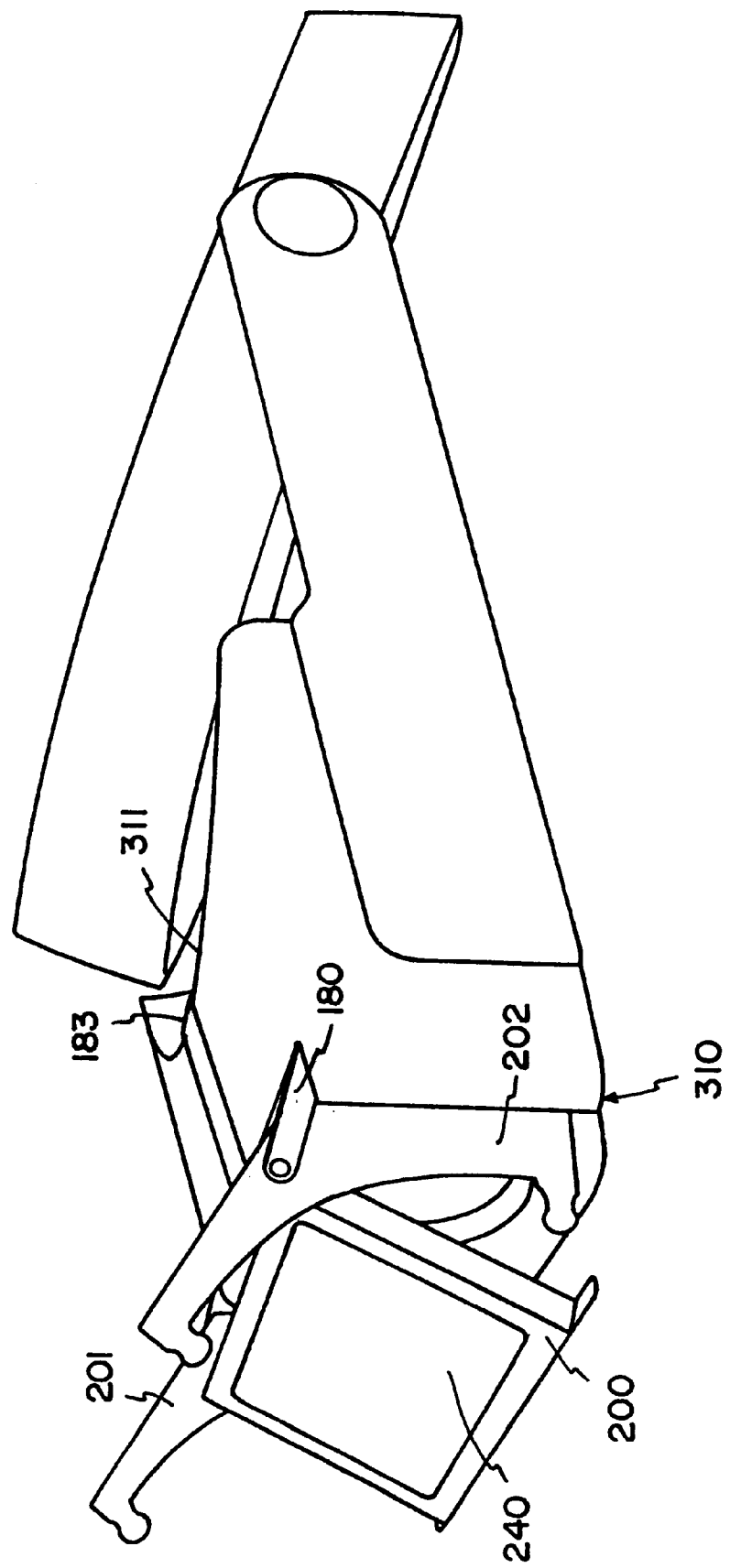
FIG. 3 illustrates an example embodiment of the present invention attached to a magnifying visor.

FIG. 3 illustrates the one example embodiment of the present invention attached to an image magnifying visor. In this example embodiment, the present invention is attachable to the OPTIVISOR™ manufactured and sold by Donegan Optical Co. of Lenexa, Kans. The design of this particular visor is described in U.S. Pat. No. 3,325,824, which is incorporated herein by reference. When in use, the user wears the OPTIVISOR on his or her head to magnify the image of the item of interest. The user can push the filter frame into the stowed position attached to the outward support arms. The user adjusts the OPTIVISOR so his or her field of view is through the two magnifying lens.

The apparatus is secured to the image magnifying visor by hooking the attachment tabs 185 and 186 around a bottom edge of the visor 310 and pushing the apparatus upward as far as possible. When the visor in place, the mounting clip 180 is rotated into place such that the projection member 184 is generally parallel with a top surface of the visor. The clipping device 183 is then pushed around the back edge of the visor 311 until the clipping device 183 engages the back edge of the visor 311. The combination of the attachment tabs 185 and 186 and the clipping device 183 will hold the apparatus in place.

When the user begins welding, a torch is typically located in one hand and a poker is located in the other hand. When platinum is welded, the image will become extremely bright as the torch heats the platinum. At this point in time, the user can move the filter frame and screen from the stowed position to the deployed position to place the filter screen within the useris line of sight through the magnifying lens. The restraining tabs are arranged using the frictional restraining force such that the tabs will become dislodged from the pair of mating tabs when the user quickly isnapsi the visor downward by simply moving his or her head (e.g., a nodding type motion). Once dislodged, the filter frame will pivot downward until the mating tabs engage the restraining tabs at the other end of the support arms. Once engaged, the filter frame will remain in place in the deployed position, holding the filter frame within the line of sight of the magnified image. The above arrangement allows the user to move the filter frame into the deployed position without requiring that either the poker or the torch be set down as the welding process continues.

FIG. 4 illustrates a schematic diagram of an example embodiment of the present invention. This embodiment of the present invention shows the apparatus constructed from thin gauge stainless steel. The individual pieces of the present invention comprise the attachment bracket with protruding support arms as a single piece of stainless steel cut from one piece of material. This combination can be bent into its appropriate shape.

Similarly, the filter frame is cut from a single piece of stainless steel. This piece can be the same piece of stainless steel used to supply the attachment bracket/support arms device discussed above. Alternatively, the filter frame can be art from a separate piece of material which is different from the bracket/support arm device. Stainless steel has been chosen to provide a durable material which can be used in the harsh welding environment. The support arms and filter frame can also be constructed from other metals, which are both durable and economical to fabricate, as well as injection-molded synthetic materials should the economies of scale permit the set up costs to be practically absorbed.

The stainless steel filter frame is bent into shape around a piece of welding screen material. In one particular embodiment, this filter screen is constructed using welding shade number 6 material. The screen material is held in place by the folded edges of the stainless steel filter frame. Alternatively, the screen can be held in place using epoxy or other adhesive material.

The filter frame, once assembled, is rotatably coupled to the assembled support arm members. In the embodiment shown in FIG. 4, the coupling tabs of the filter frame are inserted within the support holes in each support arm. The tab rotates within this hole as the filter unit is moved between its stowed, deployed, and stored positions.

The various embodiments described above are provided by way of illustration only and are not intended to limit the invention. Those skilled in the art will readily recognize various modifications and changes that may be made to the present invention without strictly following the example embodiments and applications illustrated and described herein. The scope of the present invention is set forth within the following claims.

We claim:

1. An eye-protection apparatus of the type for attachment to an image magnifying visor, comprising:
   a) a pair of support arms, the arms having a first end, a second end, and comprising projection members between the first and second end and having a pair of tabs located on the distal end thereof and a second pair of tabs on or proximate the second end of each support arm;
   b) a flip-down eye filter having a first and a second edge, and also having a pair of tabs located on the filter on or proximate the second edge, wherein the filter is rotatably coupled to the support arms on or proximate the first end of each arm at the first edge, wherein the first pair of tabs engage the pair of filter tabs to secure the filter in a stowed position; and wherein the second pair of tabs engage the pair of filter tabs to secure the filter in a deployed position; and
   c) a bracket coupled to the support arms to attach the filter and support arms to the visor;
   wherein the bracket comprises:
      a moveable u-shaped mounting clip having a pair of through-holes about each end of a clip for coupling the mounting clip to the pair of support arms;
      a projection member coupled at a first end to the mounting clip about a position between the pair of support arms, the projection member extends away from the mounting clip; and
      a clipping device coupled to a second end of the projection member for securing the bracket to the visor.

2. The apparatus according to claim 1, wherein the filter comprises a no. 6 shade welding filter plate.

3. The apparatus according to claim 1, wherein the projection members extend outward and upward from the support arms in which an angle between the top of the projection member and the support arm is at least 90 degrees.

4. The apparatus according to claim 1, wherein the projection members extend outward and upward from the first end of the support arms in which an angle between the top of the projection member and the support arm is at least 135 degrees.

5. The apparatus according to claim 1, wherein the projection members extend outward and upward from the support arms in which an angle between the top of the projection member and the support arm is at 135 degrees.

6. An eye-protection apparatus for attachment to an image magnifying visor having a magnifying lens for use by an operator when welding jewelry, comprising:
   a pair of support arms, the arms having a first end, a second end, and comprising projection members attached to the arms between the first and second end and having a pair of tabs located on the distal end thereof and a second pair of tabs on or proximate the second end of each support arm wherein the second end extends both outward and upward from the first end;
   a flip-down eye filter, the filter, having a first and a second edge, a pair of tabs located on opposite sides on the filter about the second edge, and a darkened shade welding filter plate suitable for use in welding platinum,
      wherein the eye filter is coupled to the support arms on or proximate the top side of the first end of each arm on opposite sides of the filter at the first edge,
      wherein the first pair of tabs engage the pair of filter tabs to secure the filter in a stowed position,
      wherein the second pair of tabs engage the pair of filter tabs to secure the filter in a deployed position, and
      wherein the filter can be moved from the stowed position to the deployed position without the use of the hands of the operator by quickly moving the support arms downward with a snap of the visor while being worn; and
   a bracket coupled to the support arms to attach the filter and support arms to the visor;
   wherein the bracket comprises:
      a moveable u-shaped mounting clip having a pair of through-holes about each end of a clip for coupling the mounting clip to the pair of support arms;
      a projection member coupled at a first end to the mounting clip about a position between the pair of support arms, the projection member extends away from the mounting clip; and
      a clipping device coupled to a second end of the projection member for securing the bracket to the visor;
      wherein the deployed position places the filter within the operator's field of view through the magnifying lens, and
      wherein the stowed position places the filter out of the operator's field of view through the magnifying lens,
      wherein the deployed position places the filter within the operator's field of view through the magnifying lens, and
   wherein the stowed position places the filter out of the operator's field of view through the magnifying lens.

7. The apparatus according to claim 6, wherein the projection members extend outward and upward from the support arms in which an angle between the top of the projection member and the support arm is at 135 degrees.

* * * * *